(12) United States Patent
Buchholz et al.

(10) Patent No.: US 6,479,661 B1
(45) Date of Patent: *Nov. 12, 2002

(54) METHOD FOR SYMMETRICALLY AND ASYMMETRICALLY DISUBSTITUTING CARBOXYLIC ACID AMIDES WITH ORGANOTITANATES AND GRIGNARD REAGENTS

(75) Inventors: Herwig Buchholz, Frankfurt; Urs Welz-Biermann, Mannheim; Armin Meijere; Vladimir Chaplinski, both of Göttingen, all of (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/719,971

(22) PCT Filed: Jun. 18, 1999

(86) PCT No.: PCT/EP99/04253

§ 371 (c)(1),
(2), (4) Date: Mar. 23, 2001

(87) PCT Pub. No.: WO99/65861

PCT Pub. Date: Dec. 23, 1999

(30) Foreign Application Priority Data

Jun. 18, 1998 (DE) ......................................... 198 27 167
Sep. 29, 1998 (DE) ......................................... 198 44 194

(51) Int. Cl.⁷ ........................ C07C 209/66; B01J 21/06; C07D 211/14
(52) U.S. Cl. ....................... 546/192; 564/215; 564/391; 564/414; 564/455
(58) Field of Search .......................... 546/192; 564/215, 564/391, 414, 455

(56) References Cited

PUBLICATIONS

Kuffner F. et al.: "Ueber hochverzweigte aliphatische Verbindungen" Monatshefte Fuer Chemie, Bd. 93, 1962, Seiten 496–475, XP002117676 in der Anmeldung erwaehnt.
Manfred T. Reetz et al.: "Chemoselective addition of organotitanium reagents to carbonyl compounds" Chemische Berichte., Bd. 118, Nr. 4, 1985, Seiten 1421–1440, XP002117770 Verlag Chemie GMBH.
Yuying C. Hwang et al.: "A synthesis of &–substituted amines" Journal of Organic Chemistry., Bd. 50, Nr. 20, 1985, Seiten 3885–3890, XP002117673 Easton US.
Vladimir Chaplinski et al.: "A new versatile reagent for the synthesis of cyclopropylamines . . . " Synlett.,1997, Seiten 111–114, XP002117679 Thieme Verlag, Stuttgart., DE ISSN: 0936–5214.
"Beilsteins Handbuch der Organischen Chemie, vierte Auflage, drittes und viertes Ergaenzungswerk, Bd 20, erster Teil, S. 316" 1977, Springer–Verlag, Berlin.Heidelberg.New York XP002117681 Seite 316, Absatz 3.
"Houben–Weyl, Methoden der Organischen Chemie, vol. XI/1, S. 820–823" 1957, Georg Thieme Verlag, Stuttgart, DE XP002117680 Seite 820, Absatz 2–Seite 823, Absatz 1.
Jerry March: "Advanced organic chemistry" 1985, John Wiley, New York. Chischester. Brisbane. Toronto. Singapore XP002117736 Seite 825, Absatz 3.

*Primary Examiner*—Evelyn Mei Huang

(57) ABSTRACT

The invention relates to a method for disubstituting carboxylic acid amides on a geminal carbonyl-C-atom using a Grignard reagent in the presence of an organotitanate.

19 Claims, No Drawings

METHOD FOR SYMMETRICALLY AND ASYMMETRICALLY DISUBSTITUTING CARBOXYLIC ACID AMIDES WITH ORGANOTITANATES AND GRIGNARD REAGENTS

This application is a 371 of PCT/EP 99/04253 filed on Jun. 18, 1999.

The present invention relates to a process for disubstituting carboxamides using a Grignard reagent in the presence of organotitanium compounds.

It is already known from the prior art, in particular the publication in Monatsheften Chem. 93, pages 469 to 475 (1962), that asymmetric alkylated amines are obtained in the reaction of carboxamides such as formamide with two different Grignard reagents. The yield of these products is so low (at most 15%) that these reaction products can only be referred to as byproducts.

It is also known from the prior art, in particular from Collect. Czech. Chem. Commun. 1939, 11, 506 and 1959, 24, 110, that the symmetric dialkylation of carboxamides with a Grignard reagent can give amines, the yields of which,,however, are not satisfactory.

Accordingly, it was the object of the invention to prepare symmetrically and asymmetrically substituted amino compounds with a considerably improved yield by reacting carboxamides with Grignard reagents.

Using the process according to the invention, it is possible to prepare symmetrically or asymmetrically substituted amino compounds with considerably improved yields.

Accordingly, the present invention provides a process for preparing compounds of the general formula (I)

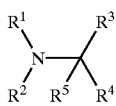
(I)

in which
$R^1$, $R^2$ and $R^3$ independently of one another are H, A, Ar, $-Si(R^6)_3$, $-Sn(R^6)_3$, $-SR^7$, $-OR^7$, $-NR^8R^9$ or $R^1$ and $R^2$ or $R^1$ and $R^3$ or $R^8$ and $R^9$ can be attached to one another and together form a cyclic ring having 3 to 8 C atoms which, optionally contains, in addition to nitrogen, at least one further heteroatom selected from the group consisting of $-S-$, $-O-$ and $-NR^6-$,
$R^4$ and $R^5$ are identical or different and are A, Ar, $-Si(R^6)_3$, $-Sn(R^6)_3$, $-SR^7$, $-OR^7$, $-NR^8R^9$, in which $R^8$ and $R^9$ are as defined above or $R^8$ and $R^9$ are attached to one another and together form a cyclic ring having 3 to 8 C atoms which optionally contains, in addition to one nitrogen atom, at least one heteroatom selected from the group consisting of $-S-$, $-O-$ and $-NR^6-$; with the proviso that $R^4$ and $R^5$ in the β position have at most one hydrogen atom,
$R^6$, $R^7$, $R^8$ and $R^9$ independently of one another are A or Ar,
A is a straight-chain or branched alkyl radical having from 1 to 10 C atoms, a straight-chain or branched alkenyl radical having 2 to 10 C atoms, or a straight-chain or branched alkynyl radical having 2–10 C atoms or a substituted or unsubstituted cycloalkyl radical having 3–8 C atoms, or a mono- or polyunsaturated cycloalkyl radical having 3–8 C atoms, and unsubstituted cycloalkyl radical having 3–8 C atoms, or a mono- or polyunsaturated cycloalkyl radial having 6–20 C atoms, and
Ar is a substituted or unsubstituted aryl radical having 6–20 C atoms, characterized in that a compound of the general formula (II)

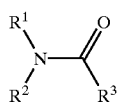
(II)

in which $R^1$, $R^2$ and $R^3$ have the meanings given above for the formula (I) is reacted with a nucleophilic reagent of the general formula (III)

(III)

in which
$R^4$ has the meaning given for the formula (I), and
Z is Li or MgX where
X is Hal and
Hal is Cl, Br or I.

According to the invention, the process is carried out in the presence of an organotitanate of the general formula (IV):

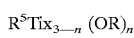
(IV)

in which
$R^5$ has the meaning given for the formula (I), and
X is Cl, Br, I and
R is alkyl having 1 to 10 C atoms or aryl having 6 to 20 C atoms,
n is an integer from 1 to 3.

Preference is given to using organotitanates in which R is isopropyl. Particular preference is given to using ethyl-, phenyl-, cyclopropyl- or p-fluorophenyl-triisopropyltitanate.

Thus, the invention also provides a process, which is characterized in that
 a) a carboxamide of the general formula (II) and an organotitanate are initially charged at room temperature under an atmosphere of inert gas in a solvent selected from the group consisting of toluene, THF, n-hexane, benzene and diethyl ether,
 b) a solution comprising a nucleophilic reagent of the general formula (III) is added dropwise and
 c) the mixture is allowed to react with stirring and, after the reaction has ended, worked up in a customary manner.

Experiments have shown that, using a nucleophilic reagent of the general formula (III), which may be a Grignard reagent and which is added as such to the reaction mixture, it is possible to convert carboxamides of the general formula (II) in the presence of organotitanates in a simple manner into symmetrically or asymmetrically substituted compounds of the general formula (I).

According to the invention, using the process described herein, it is possible to convert, with good yields, carboxamides of the general formula (II) in which $R^1$, $R^2$ and $R^3$ independently of one another can have the following meanings:
 H or
 A i.e. branched or unbranched alkyl having 1–10 C atoms, such as methyl, ethyl, n- or isopropyl, n-, sec- or t-butyl, pentyl, hexyl, heptyl, octyl, nonyl, decyl and suitable isomers thereof, or cycloalkyl having 3–8 C atoms, such as cyclopropyli cyclobutyl, cyclopentyl, cyclohexyl, cycloheptyl, cyclooctyl, and corresponding methyl- or ethyl-substituted cycloalkyl groups, or mono- or polyunsaturated cycloalkyl groups, such as cyclopentenyl or cyclopentadienyl, or branched or unbranched alkenyl having 2 to 10 C atoms, such as allyl, vinyl, isopropenyl, propenyl, or branched or unbranched alkynyl having 2 to 10 C atoms, such as ethynyl, propynyl, or aryl having 6 to 20 C atoms which is either unsubstituted or mono- or polysubstituted, such as phenyl, naphthyl, anthryl, phenanthryl, mono- or polysubstituted by substituents selected from the a group-consisting of $NO_2$, F, Cl, Br, $NH_2$, NHA, $NA_2$, OH and OA, where A can have the meanings given above, can be mono-, poly-, or fully halogenated, preferably fluorinated, or aralkenyl or aralkynyl, where the aryl, alkenyl and alkynyl groups can in each case have the given meanings, such as, for example, in phenylethynyl.

Good yields are in particular also obtained using carboxamides in which $R^1$ and $R^2$ or $R^1$ and $R^3$ together form a cyclic ring having 3–8 C atoms which, in addition to nitrogen, contains further heteroatoms, such as —S—, —O— or —$NR^6$—. Particular preference is given here to compounds in which $R^1$ and $R^2$ or $R^1$ and $R^3$ form a simple cyclic ring which includes the nitrogen of the carboxamide or in which $R^1$ and $R^2$ or $R^1$ and $R^3$ form a cyclic ring which contains, as further heteroatom, an oxygen atom. Thus, high yields are obtained in this manner when the starting materials used are compounds such as, for example,

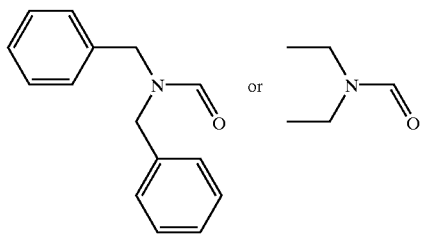

The nucleophilic reagent used can be a Grignard reagent or an organolithium compound of the general formula (III) in combination with organotitanates of the general formula (IV), in which the radicals $R^4$ and $R^5$ are preferably an alkyl radical having 1 to 10 C atoms, such as methyl, isopropyl, iso- or tert-butyl, pentyl, hexyl, heptyl, octyl, nonyl, decyl and suitable isomers thereof, or cycloalkyl having 3–8 C atoms, such as cyclopropyl, cyclobutyl, cyclopentyl, cyclohexyl, cycloheptyl, cyclooctyl or corresponding methyl- or ethyl-substituted cycloalkyl groups or mono- or polyunsaturated cycloalkyl groups, such as cyclopentenyl or cyclopentadienyl, or branched or unbranched alkenyl having 2 to 10 C atoms, such as allyl, isopropenyl, propenyl, or branched or unbranched alkynyl having 2 to 10 C atoms, such as ethynyl, propynyl, or are an aryl radical having 6 to 20 C atoms which is either unsubstituted or mono- or polysubstituted, such as phenyl, napthyl, anthryl, phenanthryl, mono- or polysubstituted by substituents selected from the group consisting of $NO_2$, F, Cl, Br, $NH_2$, NHA, $NA_2$, OH and OA, where A can have the meanings given above, can be mono-, poly- or fully halogenated, preferably fluorinated, or are an aralkyl radical having 7 to 20 C atoms, such as benzyl, optionally mono- or polysubstituted by substituents selected from the group consisting of $NO_2$, F, Cl, Br, $NH_2$, NHA, $NA_2$, OH and OA, where A can have the meanings given above, can be mono-, poly- or fully halogenated, preferably fluorinated, are an aralkenyl or aralkynyl radical, where the aryl, alkenyl and alkynyl group can in each case have the given meanings, such as, for example, in phenylethynyl.

Furthermore, the radicals $R^4$ and $R^5$ in the general formulae (III) and (IV) can be —$Si(R^6)_3$, —$Sn(R^6)_3$, —$SR^7$, —$OR^7$, —$NR^8R^9$, in which $R^6$, $R^7$, $R^8$ and $R^9$ independently of one another have the abovementioned meanings or $R^8$ and $R^9$ are attached to one another and together form a cyclic ring having 3 to 8 C atoms which may optionally, in addition to a nitrogen atom, contain at least one heteroatom selected from the group consisting of —S—, —O— and $NR^6$—.

The radical Z in the general formula (III) preferably represents a radical MgX where X is Cl or Br, or the radical Z is lithium.

Particular preference according to the invention is given to using Grignard reagents such as: methylmagnesium bromide, isopropylmagnesium bromide, iso- or tert-butylmagnesium bromide, cyclopropylmagnesium bromide, cyclohexylmagnesium chloride, allylmagnesium bromide, cyclopentylmagnesium bromide, cyclopentylmagnesium chloride, phenylmagnesium chloride, p-fluorophenylmagnesium bromide, for the reaction.

As can be demonstrated using examples, under favourable conditions a complete, conversion of the carboxamide according to the general equation (Eq. 1) has taken place:

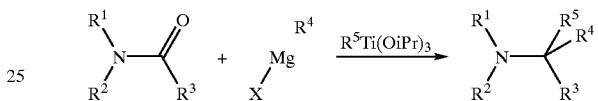

For carrying out the process according to the invention, the organotitanate, preferably organotitanium triisopropoxide, is used as a solution in a suitable solvent, which is dried beforehand. Suitable solvents are, for example aliphatic or aromatic hydrocarbons or ethers. Preference is given to using solvents selected from the group consisting of toluene, THF, n-hexane, benzene and diethyl ether, which are dried prior to the reaction by methods known to the person skilled in the art. Drying can be-carried out with the aid of magnesium sulphate, calcium chloride, sodium, potassium hydroxide or by other methods.

A preferred embodiment of the process according to the invention comprises initially charging the organotitanium triisopropoxide used in an amount of from 0.7 to 1.3, preferably 0.9 to 1.1, equvalents, based on one mol of the amide used as starting material, in the form of a solution adjusted to a temperature of from 10 to 30° C., preferably 15–25° C., particularly preferably to a temperature of about 20° C. Under an atmosphere of inert gas (nitrogen or argon), the starting material, either as such in liquid form or dissolved in a solvent selected from the group consisting of toluene, THF, n-hexane, benzene and diethyl ether, is slowly added dropwise with stirring. The reaction mixture obtained is stirred for a short period, i.e. for a few minutes, at a constant temperature. Such an amount of the nucleophilic reagent of the general formula (III), in particular Grignard reagent, is then slowly added to the resulting reaction mixture that substitution of the geminal carbonyl C atom by two identical or different substituents, i.e. a symmetric or asymmetric substitution of the geminal carbonyl C atom, can take place. The addition of a nucleophilic reagent according to the invention prepared by methods generally known to the person skilled in the art should take place at such a rate that the temperature of the reaction mixture does not exceed 50° C. It is advantageous to carry out the addition of the nucleophilic reagent, i.e. of the Grignard reagent or the lithium compound, with efficient mixing, preferably vigorous stirring. To shift the reaction equilibrium to the side of the desired symmetrically or asymmetrically substituted product, the nucleophilic reagent used, preferably Grignard reagent, is added in an amount of from 0.7 to 1.3 mol per mole of starting material that participates in the reaction.

Preference is given to adding the Grignard reagent in an amount of from 0.9 to 1.1 mol, based on 1 mol of starting material and in the same amount as the organotitanate.

After the addition of the Grignard reagent has ended, the reaction mixture is stirred for some time at a constant temperature, until the reaction is brought to completion.

Thus, by the synthesis according to the invention it is possible to prepare symmetrically and asymmetrically substituted amino compounds of the general formula (I) with good or satisfactory yields within adequate reaction times.

For example, 5 mmol of starting material are, at 20° C. and under an atmosphere of inert gas, added dropwise with stirring to a solution of 5.5 mmol of organotitanium triisopropoxide in 40 ml of dried tetrahydrofuran. The mixture is stirred at 20° C. for 5 minutes, and a solution of 5.5 mmol of a Grignard reagent are then added at such a rate that the temperature of the reaction mixture does not exceed 50° C. Stirring is continued until the reaction has gone to completion.

After the reaction according to the invention, work-up of the reaction mixture can be carried out in a manner known to the person skilled in the art.

Here, the products can be precipitated as salts using solutions of hydrochloric acid, for example a 1 molar ethereal solution of hydrochloric acid, and be filtered off and, if required, purified by recrystallization.

To remove the Lewis acid, it is possible, for example, to add a suitable amount of saturated ammonium chloride solution and water, followed by further vigorous stirring for a plurality of hours (1–3 hours). The resulting precipitate is separated off and washed with a little ether, preferably diethyl ether. The filtrate is made alkaline (pH>10) by addition of a suitable base, such as an NaOH, KOH, sodium carbonate or potassium carbonate solution, preferably sodium hydroxide solution. The phases that are formed are then separated, and the aqueous phase is extracted repeatedly (for example in the special case given above three times with in each case 30 ml) with diethyl ether. The combined organic phases are washed with (for example 15 ml of) saturated sodium chloride solution and can be dried over potassium carbonate, magnesium sulphate or sodium sulphate and filtered.

The products can be purified by various routes using methods known to the person skilled in the art, such as, for example, in the following manner:

1. They are precipitated as hydrochlorides using 1 M ethereal hydrochloric acid solution and filtered off (the resulting product is, if required, purified by recrystallization).
2. The organic phase, is extracted repeatedly with a 0.5 M acid solution, preferably an. aqueous hydrochloric acid solution. The extract obtained is adjusted to pH>10 using bases, preferably 2 M aqueous sodium hydroxide solution, and extracted at least once, preferably repeatedly, with diethyl ether. The resulting organic phases, which contain the reaction product, can be dried, if appropriate, over potassium carbonate, magnesium sulphate or sodium sulphate and be freed from the organic solvent under reduced pressure.
3. Furthermore, it is possible to isolate the reaction product by removing the organic solvent under reduced pressure and separating the residue that remains by column chromatography, to isolate the reaction product.

In the general description of the process procedure given above, the Grignard reagents can also be replaced by the corresponding lithium compounds. The corresponding lithium compounds, like the Grignard reagents, can be prepared by the methods generally known to the person skilled in the art, and they can be reacted according to the invention in the same manner as described above.

The compounds of the general formula (I) prepared according to the invention can be used, for example, as intermediates in the preparation of sulphur- or selenium-containing amines for the chiral catalysis of diethyl zinc syntheses (literature: Werth, Thomas; Tetrahydron Lett. 36; 1995, 7849–7852, Werth, Thomas et al. Helv. Chim. Acta 79, 1996, 1957–1966).

To illustrate and better understand the present invention, examples are given below. However, owing to the general validity of the described principle of the invention, they are not meant to reduce the scope of the present application to just these examples.

EXAMPLES

Organotitanium-triisopropoxide-induced symmetric and asymmetric dialkylation of carboxamides using a Grignard reagent According to the reaction shown in Equation 1, the following reactions were carried out:

TABLE 1

$R^5Ti(OiPr)_3$-induced reaction of carboxamides with $R^4MgX$.

| No. | Amide | Product | Yield [%] | $R^4MgX$ / $R^5Ti(OiPr)_3$ | Reaction conditions |
|---|---|---|---|---|---|
| 1 | (dibenzylformamide) | (N,N-dibenzyl-1-phenylethylamine) | 93 | MeTi(OiPr)$_3$ PhMgBr | 1 Equivalent 1.1 Equivalents 15 h/25° C. |

TABLE 1-continued

R⁵Ti(OiPr)₃-induced reaction of carboxamides with R⁴MgX.

$$\underset{R^2}{\overset{R^1}{\phantom{-}}}N-\underset{R^3}{\overset{O}{\|}}C + X-Mg-R^4 \xrightarrow{R^5Ti(OiPr)_3} \underset{R^2}{\overset{R^1}{\phantom{-}}}N-\underset{R^3}{\overset{R^5}{\underset{R^4}{|}}}C$$

| No. | Amide | Product | Yield [%] | R⁴MgX/ R⁵Ti(OiPr)₃ | Reaction conditions |
|---|---|---|---|---|---|
| 2 | N,N-dibenzylformamide | N,N-dibenzyl-1-cyclopropylethylamine | 48 | MeTi(OiPr)₃ cyclopropyl-MgBr | 1 Equivalent 1.1 Equivalents 13 h/RF |
| 3 | N,N-diethylformamide | N,N-diethyl-1-phenylethylamine | 53 | PhTi(OiPr)₃ MeMgBr | 0.8 Equivalent 1.2 Equivalents 24 h/25° C. |
| 4 | 1-formylpiperidine | 1-(1-phenylethyl)piperidine | 44 | MeTi(OiPr)₃ PhMgBr | 1 Equivalent 1 Equivalent 20 h/25° C. |
| 5 | N,N-dimethylformamide | N,N-dimethyl-1-cyclopropylethylamine | 45 | MeTi(OiPr)₃ cyclopropyl-MgBr | 1 Equivalent 1.1 Equivalents 15 h/RF |
| 6 | N,N-diethylformamide | N,N-diethyl-diphenylmethylamine | 55 | PhTi(OiPr)₃ PhMgBr | 1 Equivalent 1.1 Equivalents 24 h/25° C. |
| 7 | 1-formylpiperidine | 1-(diphenylmethyl)piperidine | 40 | PhTi(OiPr)₃ PhMgBr | 1 Equivalent 1 Equivalent 24 h/25° C. |

TABLE 1-continued

R⁵Ti(OiPr)₃-induced reaction of carboxamides with R⁴MgX.

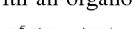

| No. | Amide | Product | Yield [%] | R⁴MgX/ R⁵Ti(OiPr)₃ | Reaction conditions |
|---|---|---|---|---|---|
| 8 | 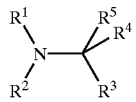 | 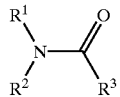 | 43 | MeTi(OiPr)₃ F-PhMgBr | 1 Equivalent 1 Equivalent 20 h/25° C. | iPr = Isopropyl, Me = Methyl, Ph = Phenyl, RF = under reflux

What is claimed is:

1. A process for preparing a compound of formula (I), $$\underset{R^2}{\overset{R^1}{\diagdown}}N-\underset{R^3}{\overset{R^5}{\diagup}}C\overset{R^4}{\diagdown} \quad (I)$$

in which
R¹ and R² are, each independently, H, A, Ar, —Si (R⁶)₃, —Sn (R⁶)₃, —SR⁷, —OR⁷ or —NR⁸R⁹,
R³ is H,
R⁴ and R⁵ are, each independently, A, Ar, —Si (R⁶)₃, —Sn (R⁶)₃, —SR⁷, —OR⁷ or —NR⁸R⁹,
R⁶, R⁷, R⁸ and R⁹ are each independently A or Ar,
A is a straight-chain or branched alkyl radical of 1 to 10 C atoms, a straight-chain or branched alkenyl radical of 2 to 10 C atoms, a substituted or unsubstituted cycloalkyl radical of 3 to 8 C atoms, or a mono- or polyunsaturated cycloalkyl radical of 3 to 8 C atoms, and
Ar is a substituted or unsubstituted aryl radical having 6 to 20 C atoms,
wherein R¹ and R² or R⁸ and R⁹ optionally form a cyclic ring having 3 to 8 C atoms which optionally has, in addition to one nitrogen atom, at least one heteroatom of —S—, —O— or —NR⁶—;
with the proviso that the radicals R⁴ and R⁵ have at most one hydrogen atom in the β position, or either one or both of R⁴ and R⁵ are cyclopropyl,
said process comprising reacting a compound of formula (II)

$$\underset{R^2}{\overset{R^1}{\diagdown}}N-\underset{R^3}{\overset{O}{\diagup\diagdown}} \quad (II)$$

in which R¹, R² and R³ have the meanings given above, with a reagent of formula (III) in a solvent

Z—R⁴   (III)

in which
R⁴ has the meaning given above,
Z is Li or MgX,
X is Hal, and
Hal is Cl, Br or I,
and with an organotitanate of formula (IV)

R⁵TiX₃₋ₙ(OR)ₙ in which
R⁵ has the meaning given above,
X is Cl, Br or I,
R is alkyl having 1 to 10 C atoms or aryl having 6 to 20 C atoms, and
n is an integer of 1 to 3.

2. A process according to claim 1, wherein
a) a carboxamide of formula (II) and an organotitanate of formula (IV) are charged at 10–30° C. under an atmosphere of inert gas in a solvent,
b) a solution comprising a nucleophilic reagent of formula (III), is added dropwise, and
c) the mixture is allowed to react while stirring.

3. A process according to claim 2, wherein charging a carboxamide and an organotitanate is carried out at about 15 to 25° C.

4. A process according to claim 2, wherein charging a carboxamide and an organotitanate is carried out at about 20° C.

5. A process according to claim 1, wherein R⁴ of the reagent of formula (III) is methyl-, cyclopropyl-, phenyl- or p-fluorophenyl.

6. A process according to claim 1, wherein the reagent of formula (III) is a Grignard reagent or an organolithium compound.

7. A process according to claim 1, wherein the reagent of formula (III) is methylmagnesium bromide, isopropylmagnesium bromide, iso- or tert-butylmagnesium bromide, cyclopropyl-magnesium bromide, cyclohexylmagnesium chloride, allylmagnesium bromide, cyclopentylmagnesium bromide, cyclopentylmagnesium chloride, phenylmagnesium chloride, or p-fluorophenylmagnesium bromide.

8. A process according to claim 1, wherein R⁵ of the organotitanate of formula (IV) is methyl, cyclopropyl, phenyl or p-fluorophenyl.

9. A process according to claim 1, wherein the organotitanate of formula (VI) is isopropyl.

10. A process according to claim 1, wherein the organotitanate of formula (IV) is methyl-, cyclopropyl-, phenyl- or p-fluorophenyl-triisopropyltitanate.

11. A process according to claim 1, wherein $R^1$ and $R^2$ of the compound of formula (II) are independently of one another H, methyl, ethyl, n- or isopropyl, iso-, sec- or tert-butyl, n-hexyl, phenyl or benzyl.

12. A process according to claim 1, wherein the cyclic ring having 3 to 8 C atoms has at least one oxygen atom.

13. A process according to claim 1, wherein the amounts of compounds (III) and (IV) are about equal.

14. A process according to claim 1, wherein the amounts of compounds (III) and (IV) are, each independently, about 0.7 to 1.3 mol equivalents to the compound of formula II.

15. A process according to claim 1, wherein the amounts of compounds (III) and (IV) are, each independently, about 0.9 to 1.1 mol equivalents to the compound of formula II.

16. A process according to claim 1, wherein the solvent is an aliphatic or aromatic hydrocarbon or ether.

17. A process according to claim 1, wherein the solvent is toluene, n-hexane, cyclohexane, benzene or diethyl ether.

18. A process according to claim 1, further comprising precipitating, extracting, or separating a compound of formula (I) by column chromatography and optionally purifying by recrystallization.

19. A process according to claim 1, further comprising the step of using the compound of formula (I) as an intermediate in the preparation of sulfur- or selenium-containing amines for the chiral catalysis of diethyl zinc syntheses.

* * * * *

UNITED STATES PATENT AND TRADEMARK OFFICE
CERTIFICATE OF CORRECTION

PATENT NO.    : 6,479,661 B1
DATED         : November 12, 2002
INVENTOR(S)   : Herwig Buchholz et al.

It is certified that error appears in the above-identified patent and that said Letters Patent is hereby corrected as shown below:

Column 11,
Line 1, reads "the organotitanate" should read -- the R of the organotitanate --

Signed and Sealed this

Twenty-second Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO.   : 6,479,661 B1
DATED        : November 12, 2002
INVENTOR(S)  : Herwig Buchholz et al.

It is certified that error appears in the above-identified patent and that said Letters Patent is hereby corrected as shown below:

Column 11,
Line 2, change "(VI)" to -- (IV) --.

Signed and Sealed this

Thirty-first Day of August, 2004

JON W. DUDAS
*Director of the United States Patent and Trademark Office*